US010029269B2

(12) United States Patent
McNulty et al.

(10) Patent No.: US 10,029,269 B2
(45) Date of Patent: Jul. 24, 2018

(54) DISPENSING DEVICE

(71) Applicant: GOJO Industries, Inc., Akron, OH (US)

(72) Inventors: John J. McNulty, Broadview Heights, OH (US); Scott Theodore Proper, Stow, OH (US)

(73) Assignee: GOJO Industries, Inc., Akron ( * ) Notice: Subject to any disclaimer, the term of this patent is extended or adjusted under 35 U.S.C. 154(b) by 51 days.

(21) Appl. No.: 14/983,782

(22) Filed: Dec. 30, 2015

(65) Prior Publication Data

US 2016/0184851 A1  Jun. 30, 2016

Related U.S. Application Data

(60) Provisional application No. 62/097,929, filed on Dec. 30, 2014.

(51) Int. Cl.
| | |
|---|---|
| *B67D 7/06* | (2010.01) |
| *B67D 7/56* | (2010.01) |
| *B05B 12/08* | (2006.01) |
| *G01N 21/64* | (2006.01) |
| *A47K 5/12* | (2006.01) |

(52) U.S. Cl.
CPC ............ *B05B 12/08* (2013.01); *A47K 5/1217* (2013.01); *G01N 21/64* (2013.01); *G01N 2021/6497* (2013.01)

(58) Field of Classification Search
CPC ................................ B05B 12/08; G01N 21/64
USPC .......................................................... 222/23
See application file for complete search history.

(56) References Cited

U.S. PATENT DOCUMENTS

| | | | | |
|---|---|---|---|---|
| 6,293,143 B1* | 9/2001 | Denton | ................ | B41J 2/17566 250/227.11 |
| 8,269,192 B2* | 9/2012 | Dixon | ...................... | G01J 1/58 250/373 |
| 8,534,791 B2* | 9/2013 | Takata | ..................... | B41J 2/175 347/19 |
| 2008/0121838 A1* | 5/2008 | Brown | ..................... | C09J 11/06 252/79.1 |
| 2010/0149232 A1* | 6/2010 | Cai | ......................... | B41J 2/175 347/7 |
| 2014/0339462 A1* | 11/2014 | Berte' | ................. | C07D 403/12 252/79.1 |

\* cited by examiner

*Primary Examiner* — Jeremy W Carroll
(74) *Attorney, Agent, or Firm* — Cooper Legal Group, LLC (57) ABSTRACT

Among other things, a dispensing device and/or a refill container are provided. The dispensing device may comprise a dispenser component configured to dispense a refill material. A sensor component may be configured to identify an optical property (e.g., whether an optical brightener is present in the refill material) of the refill material. The dispensing device may evaluate the optical property against an optical profile to determine whether the refill material is a valid refill material (e.g., comprises the optical brightener) or an invalid refill material (e.g., does not comprise the optical brightener). Operation of the dispensing device may be enabled based upon the refill material being the valid refill material. If the refill material comprises the invalid refill material, then operation of the dispensing device may be disabled and/or a flush option (e.g., evacuating the invalid refill material from the dispensing device) may be activated.

20 Claims, 5 Drawing Sheets

DISPENSING DEVICE

CROSS-REFERENCE TO RELATED APPLICATIONS

This application claims priority to U.S. Provisional Patent Application No. 62/097,929, filed on Dec. 30, 2014, the entire disclosure of which is hereby incorporated by reference.

TECHNICAL FIELD

The current application pertains to dispensing devices for dispensing material. For example, a dispensing device may dispense refill material, such as soap or other material, based upon whether an optical property of the refill material indicates that the refill material is valid (e.g., genuine) or invalid (e.g., not genuine).

BACKGROUND

Many locations, such as hospitals, factories, restaurants, homes, etc., utilize dispensing devices to dispense material. For example, a dispensing device may dispense a liquid material, powder material, aerosol material, and/or other materials (e.g., soap, anti-bacterial gels, cleansers, disinfectants, lotions, etc.). Some dispensing devices utilize a refill material container for ease of maintenance, environmental concerns, etc. The refill material container may, for example, comprise a pump and/or nozzle mechanism that can be used by a dispensing system to dispense material from the refill material container.

A manufacturer of a material may utilize one or more distributors to install dispensing devices at various end-user locations, and to install refill material containers provided by the manufacturer into corresponding dispensing devices. The manufacturer may rely upon a distributor to install a correct and/or genuine refill material container into a dispensing device. For example, the distributor may be instructed to install the refill material container such that a dispensing device in an operating room of a hospital would dispense anti-bacterial soap known to provide a particular level of sanitization, as opposed to moisturizer.

SUMMARY

According to an embodiment, a dispensing device for dispensing a material may comprise a housing configured to receive a refill material. The dispensing device may comprise a dispenser component, a sensor component, and/or a lockout component. The dispenser component may be configured to dispense the refill material (e.g., dispense soap from a reservoir or from a refill material container). The sensor component may be configured to identify an optical property of the refill material. The lockout component may be configured to evaluate the optical property against an optical profile to determine whether the refill material is a valid refill material or an invalid refill material. In an example, electromagnetic radiation may be passed through the refill material and may be collected as altered electromagnetic radiation. An optical property, such as an electrical property (e.g., as output by the collector and corresponding to properties of the altered electromagnetic radiation), of the altered electromagnetic radiation may be evaluated against an optical profile range (e.g., a voltage range and/or a current range) to determine whether the refill material comprises an optical brightener. Responsive to the refill material being the valid refill material (e.g., the refill material comprises the optical brightener), operation of the dispenser component may be enabled. Responsive to the refill material being the invalid refill material (e.g., the refill material not comprising the optical brightener), operation of the dispenser component may be disabled.

According to an embodiment, a method of optical property detection in a dispensing device may comprise identifying an optical property present in a refill material in the dispensing device. The method may comprise evaluating the optical property against an optical profile to determine whether the refill material is a valid refill material or an invalid refill material. Responsive to the refill material being a valid refill material, operation of a dispenser component may be enabled. Responsive to the refill material being an invalid refill material, operation of the dispenser component may be disabled.

According to an embodiment, a refill container may comprise a refill material container configured to house a refill material for use in a dispensing device. The refill container may comprise a nozzle coupled to the refill material container. The nozzle may be configured to dispense the refill material from the refill material container. The refill material may comprise a hygiene material and an optical brighter.

BRIEF DESCRIPTION OF THE DRAWINGS

The embodiments set forth in the drawings are illustrative and exemplary in nature and not intended to limit the subject matter defined by the claims. The following description of the illustrative embodiments can be understood when read in conjunction with the following drawings.

DETAILED DESCRIPTION

The claimed subject matter is now described with reference to the drawings, wherein like reference numerals are generally used to refer to like elements throughout. In the following description, for purposes of explanation, numerous specific details are set forth in order to provide an understanding of the claimed subject matter. It is evident, however, that the claimed subject matter can be practiced without these specific details. In other instances, structures and devices are illustrated in block diagram form in order to facilitate describing the claimed subject matter.

Figure 1:
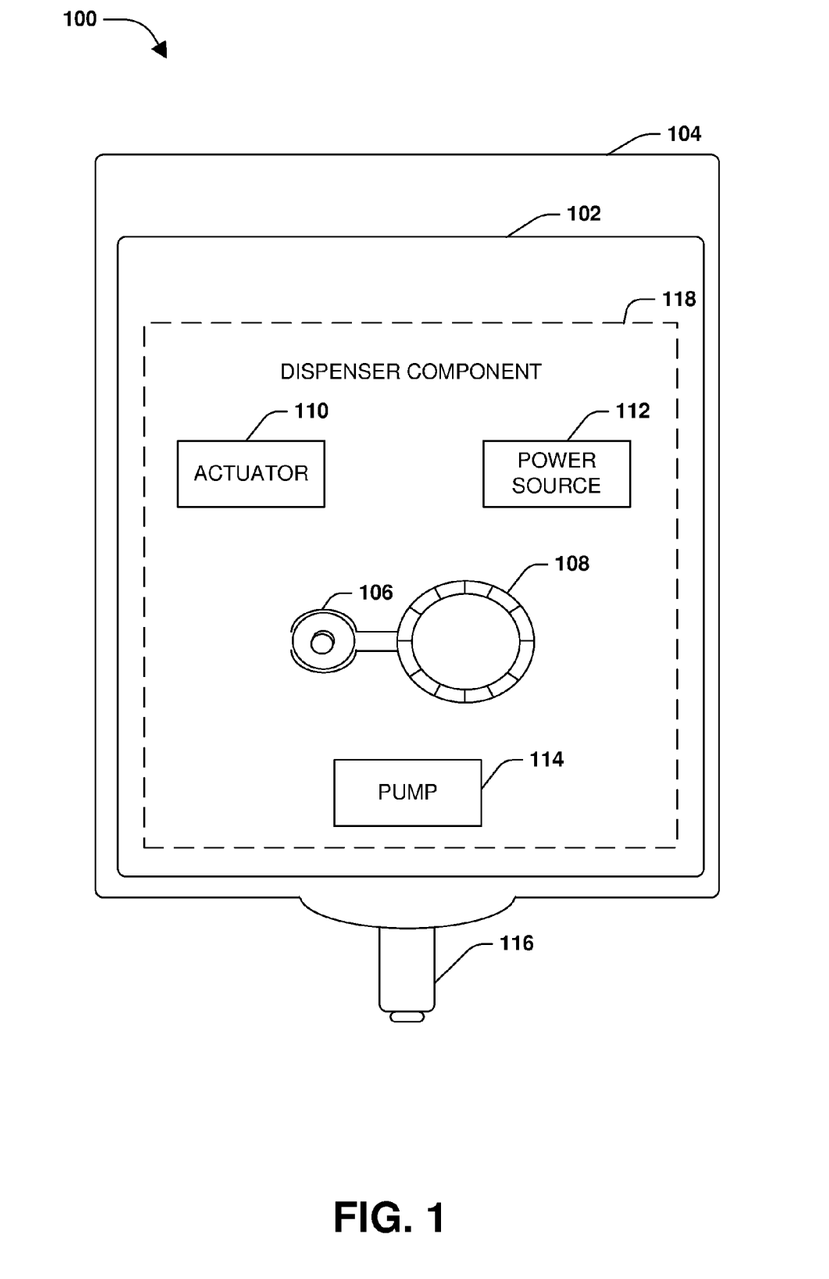
FIG. 1 is an illustration of an example dispensing device, according to some embodiments.

FIG. 1 illustrates an example of a dispensing system 100, comprising a dispensing device 104. The dispensing device 104 may comprise a housing 102 configured to hold a refill material container comprising a refill material (e.g., a liquid material, a powder material, an aerosol material, an antibacterial product, medicine, etc.). The housing 102 may comprise various mechanical and/or electrical components that facilitate operation of the dispensing device 104, such as one or more components that dispense material from the refill material container. In an example, the housing 102 may comprise a dispenser component 118. The dispenser component 118 may comprise an actuator 110, a power source 112, a motor 106, a drivetrain 108 (e.g., a gear train), and/or other components (e.g., a pump 114 and/or a dispenser nozzle 116 associated with the refill material container). The power source 112 (e.g., a battery, an AC adapter, power from a powered network communication line, etc.) may provide power to the actuator 110, the motor 106, and/or other components. The actuator 110 may be configured to detect a dispense request. The actuator 110 may be configured to invoke the motor 106 to operate the drivetrain 108 so that the pump 114 dispenses material from the refill material container through the dispenser nozzle 116 (e.g., responsive to the dispense request).

As provided herein, the dispenser component 118 may dispense the refill material if the refill material is a valid refill material (e.g., a genuine refill material comprising an optical brightener) and may refrain from dispensing the refill material if the refill material is an invalid refill material (e.g., a non-genuine refill material lacking the optical brightener). The validity of the refill material may be determined based upon an optical property of the refill material corresponding to an optical profile, such as a optical profile range specified by the optical profile (e.g., an optical brightener in the refill material may alter electromagnetic radiation that passes through the refill material relative to electromagnetic radiation that passes through a refill material that does not comprise the optical brightener).

Figure 2A:
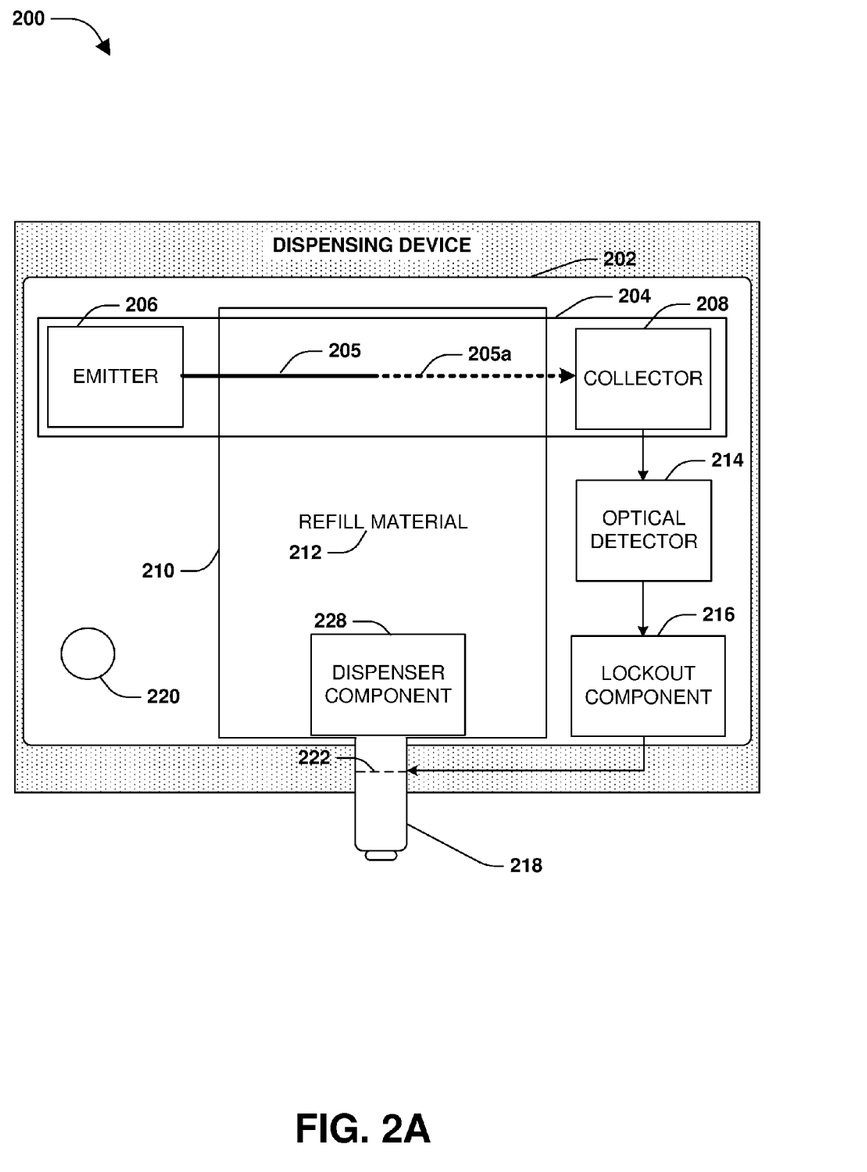
FIG. 2A is an illustration of an example dispensing device receiving an refill material comprised within a refill material container, according to some embodiments.
Figure 2B:
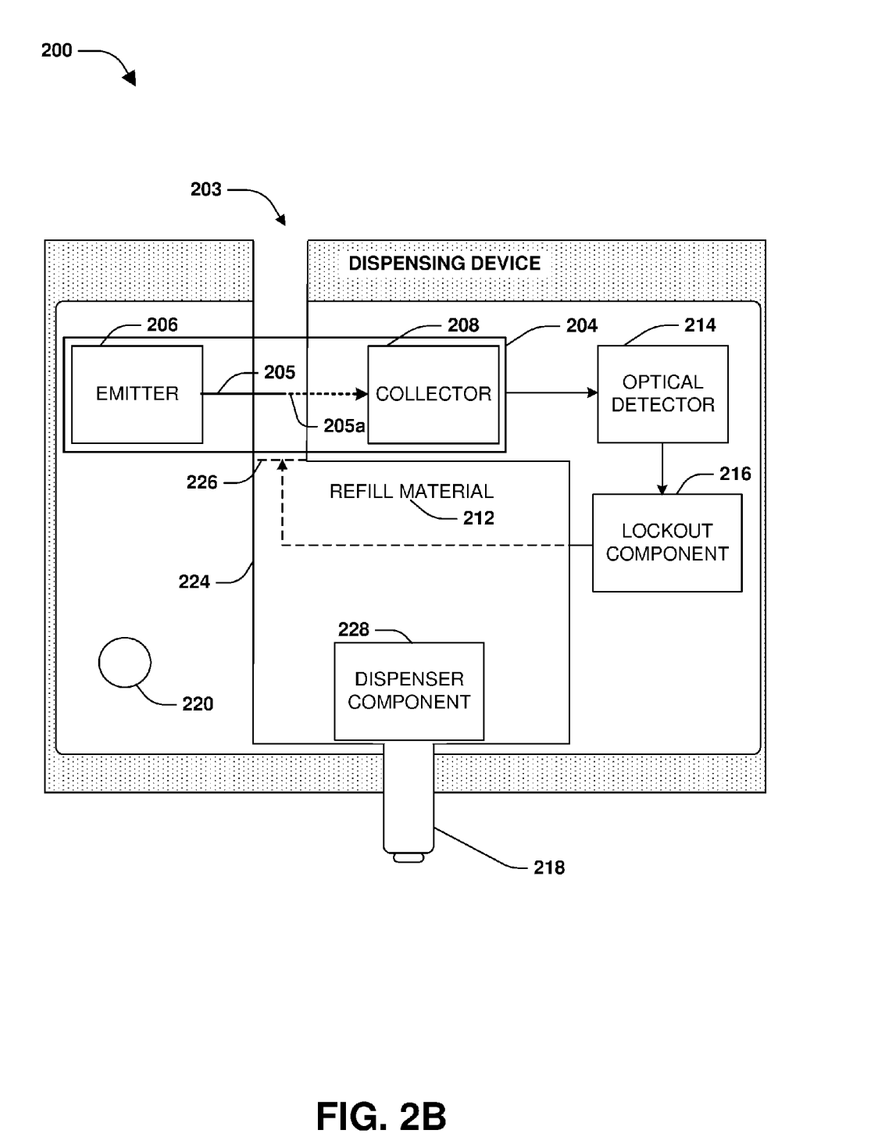
FIG. 2B is an illustration of an example dispensing device receiving a refill material, according to some embodiments.

FIGS. 2A-2B illustrate a dispensing device 200 for dispensing a refill material 212. The dispensing device 200 may comprise a housing 202. The housing 202 may be configured to receive the refill material 212 (e.g., a sanitizing substance, a hygiene material, etc.).

FIG. 2A illustrates the dispensing device 200 comprising a refill material container 210. The refill material container 210 may comprise the refill material 212 (e.g., a refill bag comprising soap), and the refill material container 210 may be installed into the housing 202. The refill material container 210 may comprise a transparent (e.g., a light permeable) container. The refill material container 210, comprising a nozzle 218, may be inserted into the housing 202. The refill material container 210 and/or the dispensing device 200 may comprise a pump and/or nozzle mechanism used to dispense the refill material 212 from the refill material container 210. For example, a dispenser component 228 may be configured to dispense the refill material 212 through the nozzle 218.

The refill material container 210 may interact with a sensor component 204. The sensor component 204 may comprise an emitter 206, a collector 208, and/or an optical detector 214. The emitter 206 may be configured to emit electromagnetic radiation 205 (e.g., a visible light signal, an ultra violet (UV) signal, an infrared (IR) signal, etc.) toward the refill material 212. The collector 208 (e.g., a photodiode) may be disposed diametrically opposite the emitter 206 relative to the refill material 212. The collector 208 may be configured to detect the electromagnetic radiation 205. The collector 208 may absorb luminescent photons from the electromagnetic radiation 205 and convert the luminescent photons into a voltage and/or a current indicative of an optical property.

The optical detector 214 may be operably coupled to the collector 208 and configured to determine a change in the optical property of the electromagnetic radiation 205 due to an interaction of the electromagnetic radiation 205 with the refill material 212 between the emitter 206 and the collector 208. In this way, the optical detector 214 may be configured to identify the optical property of the refill material 212 between the emitter 206 and the collector 208.

The collector 208 may generate a readout signal. The readout signal may be a function of the interaction of the electromagnetic radiation 205 and the refill material 212, as detected by the collector 208 (e.g., a difference in the electromagnetic radiation 205 as emitted by the emitter 206 and as collected by the collector 208). In an example, the electromagnetic radiation 205 may be altered by the interaction of the electromagnetic radiation 205 with the refill material 212, thus resulting in an altered electromagnetic radiation 205a. The controller 208 may output the altered electromagnetic radiation 205a as a voltage (e.g., a voltage measured in millivolts (mV) in the readout signal. A pulse in the readout signal, generated by the collector 208, may be indicative of the optical property. The optical property may be compared with an optical profile to determine whether the optical property (e.g., an electrical property derived from the pulse of the readout signal) is within an optical profile range (e.g., a voltage range, and/or a current range). The optical property being within the optical profile range may be indicative of an optical brightener (e.g., a chlorine based brightener) being present within the refill material 212. The optical property may be indicative of an amount of the optical brightener that is present within the refill material 212. In an example, the optical property approaching a higher end of the optical profile range, may be indicative of a higher amount of the optical brightener in the refill material 212. The optical property approaching a lower end of the optical profile range may be indicative of a lesser amount of the optical brightener in the refill material 212. In an example, the optical profile range may be between about 0.5 mV to about 1.0 mV or any other voltage.

A lockout component 216 may determine whether the optical property of the altered electromagnetic radiation 205a may be within the optical profile range, thus indicating whether the refill material 212 comprises the optical brightener (e.g., presence of the optical brightener may indicate a genuineness of the refill material 212). Responsive to the optical property (e.g., a voltage) of the altered electromagnetic radiation 205a being within the optical profile range, the refill material 212 may be determined to be a valid refill material. Based upon the refill material 212 being determined to be the valid refill material, the lockout component 216 may enable the dispenser component 228 to dispense the refill material 212.

Responsive to the optical property of the altered electromagnetic radiation 205a being outside of the optical profile range (e.g., due to a lack of optical brightener, too much optical brightener, not enough optical brightener, etc.), the refill material 212 may be determined to be an invalid refill material (e.g., not genuine). Based upon the refill material 212 being determined to be the invalid refill material, an indicator 220 may provide an invalid refill alert (e.g., a blinking light, a message sent over a network to a user interface or computer, an audio alert, a visual alert, etc.).

Based upon the refill material 212 being determined to be the invalid refill material, the lockout component 216 may disable 222 the dispenser component 228 from dispensing the refill material 212. The dispenser component 228 may be disabled 222 by disabling the nozzle 218 (e.g., sealing the refill material container 210) and/or disabling other components, such as a pump, an actuator, a motor, etc. Responsive to the lockout component 216 disabling 222 the dispenser component 228, the refill material container 210 may be removed and/or ejected (e.g., a door or cover of the housing 202 may not latch shut until the invalid refill material is removed).

FIG. 2B illustrates the dispensing device 200 comprising the housing 202 configured to receive the refill material 212 in a housing container 224 (e.g., a reservoir). The refill material 212 may be received through a shunt 203 (e.g., an opening in the housing 202) leading to the housing container 224. The sensor component 204 may be situated such that the emitter 206 may emit the electromagnetic radiation 205 towards the refill material 212 in the shunt 203 and/or in the housing container 224 (not shown). For example, the shunt 203 and/or the housing container 224 may be situated between the emitter 206 and the collector 208 so that the electromagnetic radiation 205 may pass through the refill material 212. The collector 208 may be disposed diametrically opposite the emitter 206 relative to the refill material 212. The sensor component 204 may identify the optical property of the refill material 212.

The lockout component 216 may determine whether the optical property of the altered electromagnetic radiation 205a may be within the optical profile range (e.g., if the optical property is within the optical profile range, then the refill material 212 may comprise the valid refill material, such as genuine material, otherwise, the refill material 212 may comprise the invalid refill material, such as non-genuine material). The lockout component 216 may enable the dispenser component 228 to dispense the refill material 212 based upon the refill material 212 being determined to be the valid refill material.

Based upon the refill material 212 being determined to be the invalid refill material, the indicator 220 may provide the invalid refill alert. The lockout component 216 may disable 226 the dispenser component 228 from receiving and/or dispensing the refill material 212. In an example, the shunt 203 may be disabled 226 such as being closed so that the invalid refill material may not flow into the housing container 224. In another example, the lockout component 216 may disable 222 the dispenser component 228 by disabling the nozzle 218 and/or other components such as a pump, an actuator, a motor, etc. Responsive to the lockout component 216 disabling 222 the dispenser component 228, a flush option may be activated. The flush option may be configured to evacuate the invalid refill material from the dispensing device 200. The invalid refill material may be evacuated through the nozzle 218 and/or through the shunt 203, such as by using the pump 114, as illustrated in FIG. 1.

It may be appreciated that while FIGS. 2A-2B illustrate the electromagnetic radiation 205 being emitted in a relatively linear path from the emitter 206 to the collector 208, such as the photodiode, in other embodiments, the sensor component 208 may be configured as a reflective type sensor. In a reflective type sensor, the electromagnetic radiation 205, emitted from the emitter 206, follows a relatively non-linear path to the collector 208. For example, the emitter 206 and the collector 208 may be disposed on a same side of the refill material 212, and a reflective material may be disposed on the diametrically opposite side of the refill material 212 relative to the emitter 206 and the collector 208. In such embodiments, the reflective material reflects the electromagnetic radiation 205 emitted from the emitter 206 toward the collector 208, for example.

Figure 3:
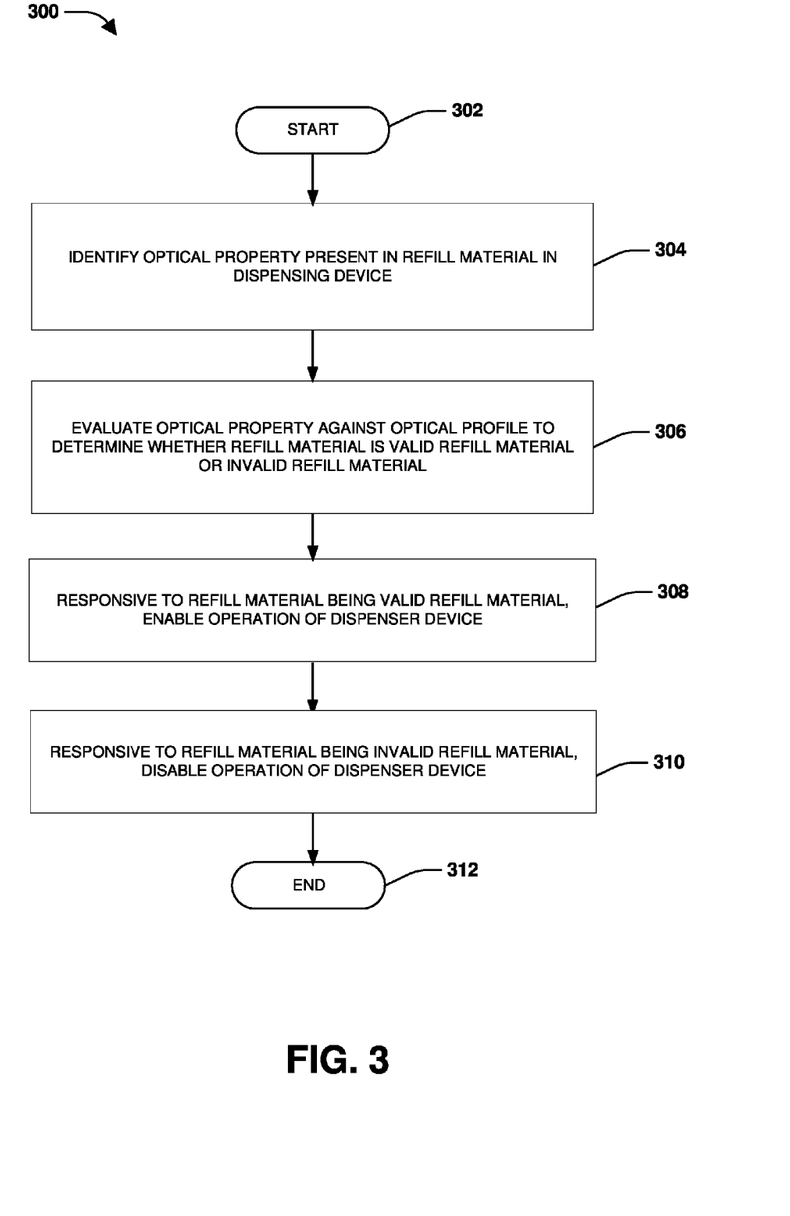
FIG. 3 is an illustration of an example method of object detection and recalibration, according to some embodiments.

FIG. 3 illustrates a method 300 of optical property detection in a dispensing device. At 302, the method 300 starts. The dispensing device may dispense a material (e.g., a sanitizing substance, a hygiene substance, etc.) utilizing a dispenser component. In an example, the material may comprise a refill material within a refill material container or within a reservoir of the dispensing device. At 304, an optical property of the refill material may be identified. The optical property may be identified by a sensor component.

At 306, the optical property may be evaluated against an optical profile to determine whether the refill material is a valid refill material or an invalid refill material. The optical property may be indicative of whether an optical brightener is present in the refill material. Responsive to the optical brightener being present above an optical brightener threshold (e.g., a threshold concentration of optical brightener detected by the sensor component based upon the optical property), the refill material may be determined to comprise the valid refill material. Responsive to the optical brightener being present below the optical brightener threshold, the refill material may be determined to comprise the invalid refill material.

At 308, responsive to the refill material being the valid refill material, operation of a dispenser component may be enabled. While enabled, the dispenser component may dispense the refill material responsive to a dispense request. At 310, responsive to the refill material being the invalid refill material, operation of the dispenser component may be disabled (e.g., the material may not be dispensed responsive to the dispense request), thus preventing the invalid material from being dispensed by the dispenser component. Responsive to the refill material being the invalid refill material, the invalid refill material may be evacuated from the dispensing device and/or an indicator may be activated to indicate that the refill material is the invalid refill material. At 312, the method 300 ends.

Figure 4:
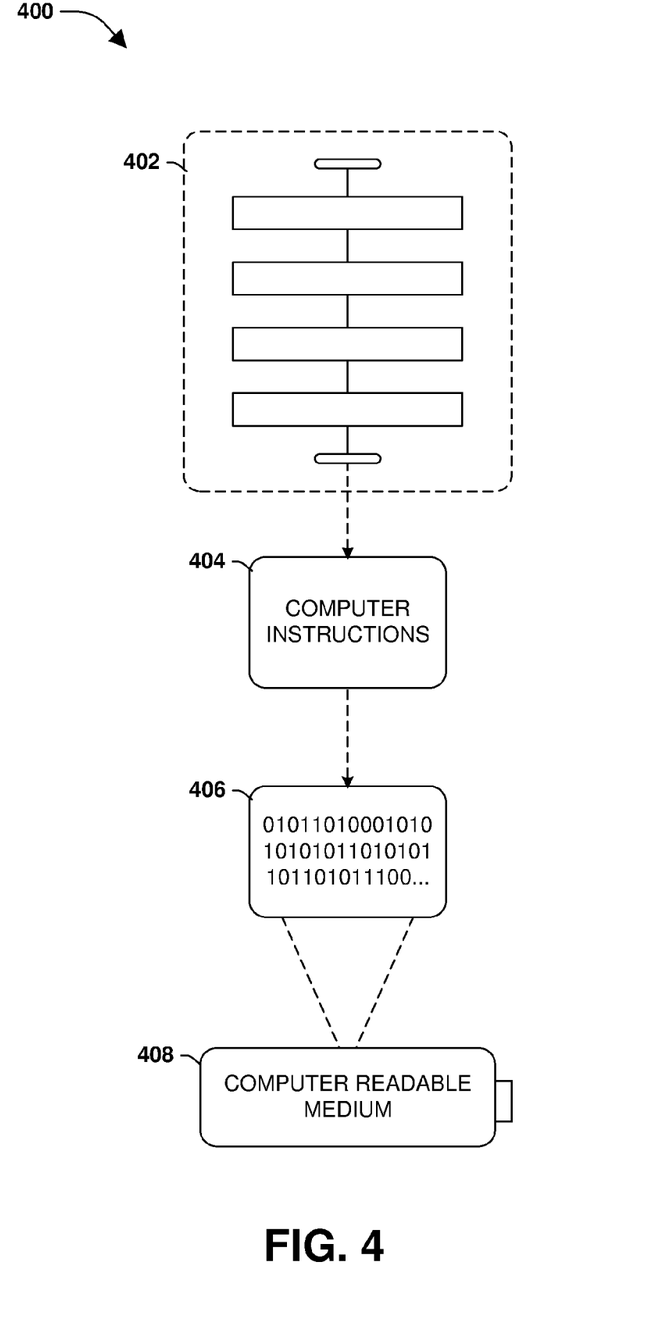
FIG. 4 is an illustration of an example computer-readable medium wherein processor-executable instructions configured to embody one or more of the provisions set forth herein may be comprised.

Still another embodiment involves a computer-readable medium comprising processor-executable instructions configured to implement one or more of the techniques presented herein. An example embodiment of a computer-readable medium or a computer-readable device that is devised in these ways is illustrated in FIG. 4, wherein the implementation 400 comprises a computer-readable medium 408, such as a CD-R, DVD-R, flash drive, a platter of a hard disk drive, etc., on which is encoded computer-readable data 406. This computer-readable data 406, such as binary data comprising at least one of a zero or a one, in turn comprises a set of computer instructions 404 configured to operate according to one or more of the principles set forth herein. In some embodiments, the processor-executable computer instructions 404 are configured to perform a method 402, such as at least some of the exemplary method 300 of FIG. 3, for example. In some embodiments, the processor-executable instructions 404 are configured to implement a system, such as at least some of the exemplary dispensing device 100 of FIG. 1, and/or at least some of the exemplary sensing device 200 of FIGS. 2A-2B, for example. Many such computer-readable media are devised by those of ordinary skill in the art that are configured to operate in accordance with the techniques presented herein.

Although the subject matter has been described in language specific to structural features or methodological acts, it is to be understood that the subject matter defined in the appended claims is not necessarily limited to the specific features or acts described above. Rather, the specific features and acts described above are disclosed as example forms of implementing at least some of the claims.

Many modifications may be made to the instant disclosure without departing from the scope or spirit of the claimed subject matter. Unless specified otherwise, "first," "second," or the like are not intended to imply a temporal aspect, a spatial aspect, an ordering, etc. Rather, such terms are merely used as identifiers, names, etc. for features, elements, items, etc. For example, a first object and a second object generally correspond to object A and object B or two different or two identical objects or the same object.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally to be construed to mean one or more unless specified otherwise or clear from context to be directed to a singular form. Also, at least one of A and B or the like generally means A or B or both A and B. Furthermore, to the extent that "includes", "having", "has", "with", or variants thereof are used in either the detailed description or the claims, such terms are intended to be inclusive in a manner similar to "comprising".

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A method of optical property detection in a dispensing device, comprising:
   identifying an optical property of a refill material in the dispensing device;
   evaluating the optical property against an optical profile to determine whether the refill material is a valid refill material or an invalid refill material, wherein:
      the refill material is determined to be the valid refill material when the evaluation of the optical property against the optical profile determines that the refill material comprises an optical brightener;
   responsive to the refill material being the valid refill material, enabling operation of the dispenser device to dispense the refill material; and
   responsive to the refill material being the invalid refill material, disabling operation of the dispenser device.

2. The method of claim 1, comprising:
   responsive to the refill material being the invalid refill material, enabling a pump within the dispensing device to evacuate the invalid refill material from the dispensing device.

3. The method of claim 1, comprising:
   responsive to the refill material being the invalid refill material, activating an indicator to indicate that the refill material is the invalid refill material.

4. The method of claim 1, the identifying comprising:
   emitting electromagnetic radiation toward the refill material; and
   detecting electromagnetic radiation traversing the refill material.

5. The method of claim 4, wherein the electromagnetic radiation emitted toward the refill material is in a visible light spectrum.

6. The method of claim 4, wherein the electromagnetic radiation emitted toward the refill material is in an ultraviolent light spectrum.

7. The method of claim 4, wherein the electromagnetic radiation emitted toward the refill material is in an infrared light spectrum.

8. The method of claim 4, the identifying comprising:
   generating an electrical signal in response to the detecting, wherein the evaluating comprises at least one of:
      comparing a voltage of the electrical signal to an expected voltage range associated with the optical profile, or
      comparing a current of the electrical signal to an expected current range associated with the optical profile.

9. The method of claim 8, the evaluating comprising at least one of:
   determining that the refill material is a valid refill material when the voltage of the electrical signal is within the expected voltage range associated with the optical profile; or
   determining that the refill material is a valid refill material when the current of the electrical signal is within the expected current range associated with the optical profile.

10. The method of claim 1, wherein the optical brightener is a chlorine-based brightener.

11. The method of claim 1, the evaluating comprising:
    determining an amount of the optical brightener present within the refill material.

12. The method of claim 1, comprising:
    detecting a dispense request, wherein the identifying and the evaluating are responsive to the detecting.

13. A method of optical property detection in a dispensing device, comprising:
    detecting a dispense request;
    emitting electromagnetic radiation toward a refill material in the dispensing device in response to the detecting;
    detecting at least some of the electromagnetic radiation after the electromagnetic radiation has traversed the refill material to generate an electrical signal;
    evaluating a optical property of the refill material against an optical profile, using the electrical signal, to determine whether the refill material is a valid refill material, wherein the refill material is determined to be the valid refill material when the evaluation of the optical property against the optical profile determines that the refill material comprises an optical brightener; and
    responsive to the refill material being the valid refill material, dispensing the refill material to satisfy the dispense request.

14. The method of claim 13, responsive to the refill material not being the valid refill material, disabling operation of the dispenser device.

15. The method of claim 14, responsive to the refill material not being the valid refill material, activating an indicator to indicate that the refill material is not the valid refill material.

16. The method of claim 13, wherein the evaluating comprises at least one of:
    comparing a voltage of the electrical signal to an expected voltage range associated with the optical profile, or comparing a current of the electrical signal to an expected current range associated with the optical profile.

17. The method of claim 13, wherein the evaluating comprises:

determining an amount of optical brightener present within the refill material.

18. A non-transitory computer readable medium comprising processor-executable instructions that when executed perform operations of optical property detection in a dispensing device, the operations comprising:

identifying an optical property of a refill material in the dispensing device;

evaluating the optical property against an optical profile to determine whether the refill material is a valid refill material or an invalid refill material, wherein:

the refill material is determined to be the valid refill material when the evaluation of the optical property against the optical profile determines that the refill material comprises an optical brightener;

responsive to the refill material being the valid refill material, enabling operation of the dispenser device to dispense the refill material; and responsive to the refill material being the invalid refill material, disabling operation of the dispenser device.

19. The non-transitory computer readable medium of claim 18, wherein the evaluating comprises:

determining an amount of optical brightener present within the refill material.

20. The non-transitory computer readable medium of claim 18, the operations comprising:

responsive to the refill material being the invalid refill material, enabling a pump within the dispensing device to evacuate the invalid refill material from the dispensing device.

* * * * *